US01263573382

(12) United States Patent
Bessant et al.

(10) Patent No.: US 12,635,733 B2
(45) Date of Patent: *May 26, 2026

(54) AEROSOL-GENERATING SYSTEM WITH ADJUSTABLE PUMP FLOW RATE

(71) Applicant: Altria Client Services LLC, Richmond, VA (US)

(72) Inventors: Michel Bessant, Carouge (CH); Ben Mazur, Bristol (GB); Eva Saade Latorre, Neuchatel (CH); Alain Tabasso, Essertines-sur-Yverdon (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/438,729

(22) Filed: Feb. 12, 2024

(65) Prior Publication Data

US 2024/0180252 A1 Jun. 6, 2024

Related U.S. Application Data

(63) Continuation of application No. 16/951,077, filed on Nov. 18, 2020, now Pat. No. 11,896,056, which is a
(Continued)

(30) Foreign Application Priority Data

Nov. 29, 2016 (EP) ..................................... 16201194

(51) Int. Cl.
*A24F 40/48* (2020.01)
*A24F 40/40* (2020.01)
(Continued)

(52) U.S. Cl.
CPC ............. *A24F 40/48* (2020.01); *A24F 40/40* (2020.01); *A24F 40/50* (2020.01); *A24F 47/00* (2013.01);
(Continued)

(58) Field of Classification Search
CPC ...................................................... A24F 40/48
See application file for complete search history.

(56) References Cited

U.S. PATENT DOCUMENTS 6,196,219 B1 * 3/2001 Hess ................ A61M 15/0085
128/200.14
10,327,479 B2 6/2019 Popplewell et al.
(Continued)

FOREIGN PATENT DOCUMENTS

EP 1618803 A1 1/2006
WO WO-2014/150552 A1 9/2014
(Continued)

OTHER PUBLICATIONS

European Search Report for European Application No. 16201194.4 Dated May 19, 2017.
(Continued)

*Primary Examiner* — Renee S Luebke
(74) *Attorney, Agent, or Firm* — Harness, Dickey & Pierce, P.L.C.

(57) ABSTRACT

A method of generating an aerosol in an aerosol-generating system includes storing liquid aerosol-forming substrate in a liquid storage portion and delivering via a pump a liquid aerosol-forming substrate from the liquid storage portion to an atomizer. The method also includes sensing a puff via a a puff sensor in an airflow path of the aerosol-generating system and determining a puff intensity during the puff via a controller. The delivery flow rate of the liquid aerosol-forming substrate to the atomizer is adjusted in response to the determined puff intensity.

10 Claims, 2 Drawing Sheets

Related U.S. Application Data continuation of application No. 16/889,043, filed on Jun. 1, 2020, now Pat. No. 10,856,571, which is a continuation of application No. 15/825,548, filed on Nov. 29, 2017, now Pat. No. 10,667,559, which is a continuation of application No. PCT/EP2017/077666, filed on Oct. 27, 2017.

(51) Int. Cl.

| | |
|---|---|
| *A24F 40/50* | (2020.01) |
| *A24F 47/00* | (2020.01) |
| *A61M 11/04* | (2006.01) |
| *A61M 15/06* | (2006.01) |
| *H05B 1/02* | (2006.01) |
| *A24F 40/10* | (2020.01) |
| *A61M 16/00* | (2006.01) |

(52) U.S. Cl.
CPC .......... *A61M 11/042* (2014.02); *A61M 15/06* (2013.01); *H05B 1/0227* (2013.01); *H05B 1/0297* (2013.01); *A24F 40/10* (2020.01); *A61M 2016/0021* (2013.01); *A61M 2016/0027* (2013.01); *A61M 2016/0039* (2013.01); *A61M 2205/3653* (2013.01); *A61M 2205/8206* (2013.01)

(56) References Cited

U.S. PATENT DOCUMENTS

| | | | | |
|---|---|---|---|---|
| 10,667,559 | B2 * | 6/2020 | Bessant | ................ H05B 1/0227 |
| 10,856,571 | B2 * | 12/2020 | Bessant | ................ A61M 15/06 |
| 11,896,056 | B2 * | 2/2024 | Bessant | ................... A24F 47/00 |
| 2010/0031967 | A1 | 2/2010 | Inagaki | |
| 2011/0079220 | A1 | 4/2011 | Altobelli et al. | |
| 2014/0300480 | A1 | 10/2014 | Xiang | |
| 2014/0338685 | A1 | 11/2014 | Amir | |
| 2015/0282527 | A1 | 10/2015 | Henry, Jr. | |
| 2016/0262454 | A1 | 9/2016 | Sears et al. | |
| 2017/0172211 | A1 | 6/2017 | Batista et al. | |
| 2017/0220424 | A1 * | 8/2017 | Doshi | ................. H04L 41/5019 |
| 2017/0224024 | A1 * | 8/2017 | Jochnowitz | ............. A24F 40/53 |
| 2017/0340009 | A1 | 11/2017 | Hon | |
| 2017/0347710 | A1 | 12/2017 | Hon | |
| 2018/0068456 | A1 * | 3/2018 | Nash | ....................... G06T 7/521 |
| 2018/0146710 | A1 | 5/2018 | Bessant et al. | |
| 2018/0168223 | A1 * | 6/2018 | Zinovik | .................. H05B 3/44 |
| 2019/0230982 | A1 | 8/2019 | Inagaki | |
| 2019/0297952 | A1 | 10/2019 | Qiu | |
| 2020/0037668 | A1 | 2/2020 | Robert et al. | |
| 2020/0046033 | A1 | 2/2020 | Robert et al. | |
| 2020/0163381 | A1 | 5/2020 | Qiu | |
| 2021/0068456 | A1 | 3/2021 | Bessant et al. | |
| 2024/0180252 | A1 * | 6/2024 | Bessant | ................... A24F 40/48 |

FOREIGN PATENT DOCUMENTS

| | | |
|---|---|---|
| WO | WO-2014/153515 A1 | 9/2014 |
| WO | WO-2017/108429 A1 | 6/2017 |
| WO | WO-2017108394 A1 | 6/2017 |

OTHER PUBLICATIONS

Written Opinion for corresponding Application No. PCT/EP2017/077666 dated Feb. 1, 2018.

* cited by examiner

AEROSOL-GENERATING SYSTEM WITH ADJUSTABLE PUMP FLOW RATE

CROSS-REFERENCE TO RELATED APPLICATIONS

This application is a continuation of U.S. application Ser. No. 16/951,077, filed on Nov. 18, 2020, issued as U.S. Pat. No. 11,896,056, which is a continuation of U.S. application Ser. No. 16/889,043, filed Jun. 1, 2020, issued as U.S. Pat. No. 10,856,571 which is a continuation of U.S. application Ser. No. 15/825,548, filed Nov. 29, 2017, issued as U.S. Pat. No. 10,667,659, which is a continuation of, and claims priority to, international application no. PCT/EP2017/077666, filed on Oct. 27, 2017, and further claims priority under 35 U.S.C. § 119 to European Patent Application No. 16201194.4, filed Nov. 29, 2016, the entire contents of each of which are incorporated herein by reference.

BACKGROUND

Field

Example embodiments relate to an aerosol-generating system (which may also be referred to as electronic vaping systems) comprising a pump, an atomizer and a puff sensor. The delivery flow rate of the pump is adjusted in response to a desired (or, alternatively predetermined) puff intensity. Example embodiments also relate to a corresponding method for generating an aerosol.

Description of Related Art

Aerosol-generating systems available may comprise a vaporizer employing a wick-and-coil arrangement. A part of a capillary wick may extend into a liquid storage portion containing e-liquid to be volatilized. Another part of the wick may be at least partially surrounded by a coil of heating wire. Upon application of an electric current, the heating wire evaporates the e-liquid contained in the wick. Dose delivery may be difficult to control as it may depend on the puff frequency of the vaper and on the capillary properties of the wick.

In another type of aerosol-generating systems a reservoir, a micropump and a vaporizer may be included. During a puff, a constant stream of e-liquid is actively pumped from the liquid storage portion to the vaporizer. The flow rate of the micropump is kept constant such that an active control of the delivered dose is achieved. In this way a homogenous delivery of nicotine during an inhaling experience is provided.

It has been noted that a vaper's preference may vary, as some vapers prefer a more intensive puffing regime than others.

SUMMARY

At least one example embodiment relates to an aerosol-generating system.

In at least one example embodiment, an aerosol-generating system comprises a housing including an air inlet and an air outlet, an airflow path defined between the air inlet and the air outlet; vaporizer configured to vaporize an aerosol-forming substrate, the vaporizer including, a heating element; a liquid storage portion configured to contain the aerosol-forming substrate; a pump configured to deliver the aerosol-forming substrate from the liquid storage portion to the vaporizer; a puff sensor in the airflow path, the puff sensor configured to sense a puff, and a controller connected to the puff sensor and to the heating element, the controller configured to determine a puff intensity based on an output from the puff sensor and adjust a delivery flow rate of the pump and the electrical power supplied to the heating element in response to the determined puff intensity.

In at least one example embodiment, the puff sensor is one of a pressure sensor or an airflow sensor.

At least one example embodiment relates to a method of generating an aerosol.

In at least one example embodiment, a method of generating an aerosol comprises pumping a liquid aerosol-forming substrate from a liquid storage portion to a vaporizer using a pump, the vaporizer including, a heating element configured to vaporize the liquid aerosol-forming substrate; sensing a puff using a puff sensor, the puff sensor in an airflow path of the aerosol-generating system, the puff sensor configured to sense a puff; and determining, using a controller, a puff intensity by comparing an output from the puff sensor with values stored in a look-up table, the controller configured to adjust a delivery flow rate of the pump and electrical power supplied to the heating element in response to the determined puff intensity.

In at least one example embodiment, the puff intensity is based on a puff sensor reading obtained after about 0.1 seconds to about 0.9 seconds after initiation of the puff.

In at least one example embodiment, the sensing includes at least one of detecting the initiation of the puff by the puff sensor, or detecting the initiation of the puff by an activating a button.

In at least one example embodiment, the method may further include adjusting the electrical power supplied to the heating element in response to the delivery flow rate of the liquid aerosol-forming substrate.

In at least one example embodiment, the method may include activating the pump until an end of the puff is detected.

In at least one example embodiment, the method may include pre-heating the heating element upon initiation of a puff.

In at least one example embodiment, the method may include activating the heating element for the duration of the puff.

In at least one example embodiment, the method may include activating the heating element for an additional predefined period of time about 0.5 seconds after the pump has been deactivated.

BRIEF DESCRIPTION OF THE DRAWINGS

Example embodiments will not be described, by way of example only.

DETAILED DESCRIPTION

Figure 1:
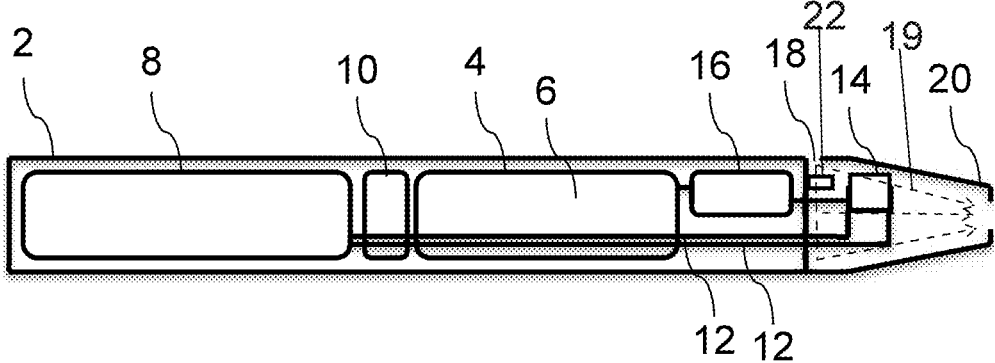
FIG. 1 is illustration of an aerosol-generating system in accordance with at least one example embodiment.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

One or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to at least one example embodiment, a method for generating an aerosol in an aerosol-generating system comprises storing a liquid aerosol-forming substrate in a liquid storage portion, delivering via a pump the liquid aerosol-forming substrate from the liquid storage portion to an atomizer, and providing a sensor in an airflow path of the aerosol-generating system. The sensor is configured to sense a puff and/or a puff intensity of the puff. The delivery flow rate of the liquid aerosol-forming substrate to the atomizer is adjusted in response to the sensed puff intensity.

The flow rate of the pump, by which the liquid-aerosol-forming substrate is delivered to the atomizer, is adjusted based on the intensity of the puff of the vaper vaping the aerosol-generating system. The aerosol composition may remain constant independent from the inhalation intensity.

Typical puff profiles taken from a plurality of vapers may share common characteristics. In particular, independent from the overall intensity of a puff, the maximum intensity of a puff is reached after about 0.3 seconds to about 0.6 seconds or about 0.5 seconds after initiation of the puff. The maximum intensity can be used as a measure of the overall intensity of the puff. Thus, the measured airflow rate or the measured pressure drop in the airflow path after about 0.3 seconds to about 0.6 seconds or about 0.5 seconds of initiation of a puff may be used as a measure for the overall puff intensity. The delivery flow rate of the pump is adjusted according to the puff intensity. The pump may be configured as a micropump.

The sensor may be configured as an airflow sensor and may measure the airflow rate. The airflow rate indicates the amount of air that is drawn through the airflow path of the aerosol-generating system per time by the vaper. Depending upon the detected airflow rate, the puff intensity may be determined. The higher the detected airflow rate is, the higher the determined puff intensity is. The airflow rate may be detected about 0.3 seconds to about 0.6 seconds or about 0.5 seconds after the initiation of the puff. The initiation of the puff may be detected by the airflow sensor when the airflow exceeds a desired (or, alternatively predetermined) threshold. Initiation may also be detected upon a vapor activating a button.

The sensor may also be configured as a pressure sensor is configured to measure the pressure of the air inside the aerosol-generating system which is drawn through the airflow path of the system by the vaper during a puff. The sensor may be configured to measure a pressure difference or pressure drop between the pressure of ambient air outside of the aerosol-generating system and of the air which is drawn through the system by the vaper. The pressure of the air may be detected at an air inlet, such as a semi-open inlet, a mouth end of the system, an aerosol formation chamber or any other passage or chamber within the aerosol-generating system, through which the air flows. When the vaper draws on the aerosol-generating system, a negative pressure or vacuum is created inside the system, wherein the negative pressure may be detected by the pressure sensor. The term "negative pressure" is to be understood as a relative pressure with respect to the pressure of ambient air. In other words, when the vaper draws on the system, the air which is drawn through the system has a pressure which is lower than the pressure off ambient air outside of the system. The air pressure is detected about 0.3 seconds to about 0.6 seconds or about 0.5 seconds after the initiation of the puff. The initiation of the puff may be detected by the pressure sensor if the pressure difference exceeds a desired (or, alternatively predetermined) threshold. Initiation may also be detected upon a vaper activating a button. The higher the detected pressure difference, i.e. the lower the pressure of the air which is drawn through the system, the higher the determined puff intensity.

The airflow rate or the pressure drop may also be continuously measured by the sensor and the puff intensity may be determined on basis of the highest airflow rate or highest pressure drop value in the course of a puff duration.

Depending upon the determined puff intensity, the delivery flow rate of the liquid aerosol-forming substrate from the pump towards the atomizer is adjusted by a controller. The flow rate of the liquid aerosol-forming substrate may be increased when a high puff intensity is determined. The flow rate of the liquid aerosol-forming substrate may be decreased when a low puff intensity is determined. The flow rate of liquid aerosol-forming substrate is a measure of the amount of liquid aerosol-forming substrate that is pumped from the liquid storage portion by the pump to the atomizer per time. In this regard, the atomizer may be operated for a desired (or, alternatively predetermined) time during the puff of a vaper. For example, the atomizer may be operated for about 0.5 seconds to about 10 seconds, about 1 second to about 4 seconds, or about 2 seconds. During this desired (or, alternatively predetermined) time, the amount of liquid aerosol-forming substrate which is pumped to the atomizer per time may be adjusted once the puff intensity is determined. Alternatively, in at least one example embodiment, the atomizer may be operated for as long as a puff lasts, i.e. as long as the vaper draws upon the aerosol-generating system. In this case, the amount of liquid aerosol-forming substrate which is pumped to the atomizer per time may be adjusted for the time during which the vaper draws upon the aerosol-generating system once the puff intensity is determined.

The atomizer is configured to atomize the liquid aerosol-forming substrate to form an aerosol, which can subsequently be inhaled by a vaper. The atomizer may comprise a heating element configured to vaporize the liquid aerosol-forming substrate, in which case the atomizer will be denoted as a vaporizer. Generally, the atomizer may be configured as any device which is able to atomize and/or vaporize the liquid aerosol-forming substrate. In at least one example embodiment, the atomizer may comprise a nebulizer or an atomizer nozzle based on the Venturi effect to atomize the liquid aerosol-forming substrate. Thus, the atomization of the liquid aerosol-forming substrate may be realized by a non-thermally aerosolization technique. A mechanically vibrating vaporizer with vibrating elements, vibrating meshes, a piezo-driven nebulizer or surface acoustic wave aerosolization may be used.

In at least one example embodiment, the atomizer may be configured as a vaporizer and the heating regime of the heating element may be additionally adjusted. The heating element may be heated faster or to a higher temperature or with a higher electric power, when a high puff intensity is determined. Consequently, if a low puff intensity is determined, the heating of the heating element is conducted slower, to a lower temperature, or with less electric power. By adjusting the heating regime of the vaporizer, the vaporization and/or aerosolization of the liquid aerosol-forming substrate may be adjusted to the puff intensity. Thereby, the vaper experiences a similar puff experience independent of the intensity, with which the vaper draws upon the system. The flow rate of the liquid aerosol-forming substrate may be adjusted together with the adjustment of the heating regime of the vaporizer, such that the puff experience of the user may be synergistically enhanced.

For determining the puff intensity and controlling the adjustment of the delivery flow rate of the liquid aerosol-forming substrate, a controller may be provided. The controller may also control the heating regime of the vaporizer. The controller may be operatively connected to the puff sensor. The controller may be operatively connected to the heating element. The controller may be configured to determine the puff intensity based on the puff sensor reading, that is, based on the detected parameter of the sensor. The controller may be configured to adjust the delivery flow rate of the pump and the electrical power supplied to the heating element in response to the determined puff intensity. In at least one example embodiment, when the sensor detects a high airflow or a large pressure difference, the controller determines a high puff intensity and increases the flow rate of the liquid aerosol-forming substrate. Additionally, the controller may increase the heating temperature of the heating element of the vaporizer.

For determining the puff intensity, predetermined airflow values and/or pressure values may be stored in a look-up table. The controller may be configured to compare the parameter values which are detected by the sensor with the values which are stored in the look-up table to determine the puff intensity. The controller may compare the value, which is detected by the sensor after about 0.3 seconds to about 0.6 seconds or about 0.5 second after the puff initiation with the values stored in the look-up table. The controller may also compare the highest airflow or pressure value, which is detected by the sensor after about 1 second, about 0.7 seconds, or about 0.5 seconds after the initiation of the puff with the values stored in the look-up table. In at least one example embodiment, the controller may compare the highest value, which is measured by the sensor during a puff duration with the values stored in the look-up table.

The controller may comprise a microprocessor, which may be a programmable microprocessor. The controller may be part of electric circuitry, comprising further electronic components. The controller may be configured to regulate a supply of power to the atomizer. Power may be supplied to the atomizer continuously following activation of the system or may be supplied intermittently, such as on a puff-by-puff basis. The power may be supplied to the atomizer in the form of pulses of electrical current. The pump may be activated until the end of a puff is detected by the sensor.

The pump may be activated for the whole duration of the puff. The heating element of the vaporizer may stay activated for an additional desired (or, alternatively predetermined) period of time, such as about 0.5 seconds after the pump is deactivated. Upon initialization of a puff, the heating element may be pre-heated to enhance the aerosol quality of the generated aerosol.

The electrical power supplied to the heating element may be adjusted by means of pulse width modulation. Hereto, a switch may be provided and used for switching between supply and load on and off at a fast rate. During use of pulse width modulation, power loss in the switch is very low. When the switch is off there is little or no current, and when it is on and power is being transferred to the vaporizer, there is almost no voltage drop across the switch. Power loss is thus in both cases very low, increasing the efficiency of the vaporizer.

According to at least one example embodiment, an aerosol-generating system is provided. The system comprises a housing with an air inlet or semi-open inlet and an air outlet, defining an airflow path there between. The system further comprises an atomizer configured to atomize an aerosol-forming substrate and a pump configured to deliver a liquid aerosol-forming substrate from a liquid storage portion to the atomizer. A puff sensor is provided located in the airflow path. The puff sensor is configured to sense a puff. A controller is configured to determine a puff intensity based on the sensed purr. The delivery flow rate of the liquid aerosol-forming substrate to the atomizer is adjusted in response to the determined puff intensity.

The atomizer of the system may comprise a heating element for vaporizing the liquid aerosol-forming substrate, in which case the atomizer will be denoted as a vaporizer.

The controller may be operatively connected to the puff sensor and to the heating element. The controller may be configured to determine the puff intensity based on the puff sensor reading. The controller may be configured to adjust the delivery flow rate of the pump and the electrical power supplied to the heating element in response to the determined puff intensity.

An adjusted amount of the liquid aerosol-forming substrate may be pumped from the liquid storage portion to a deposition region of the heating element. By depositing the liquid aerosol-forming substrate to the heating element directly, the liquid aerosol-forming substrate can remain in its liquid state until it reaches the heating element. In at least one example embodiment, few residues might be produced during liquid transport so as to allow for production of cartridges without atomizers. Due to the improved liquid transport, tubing segments and atomizers might not need to be disposed once the liquid storage portion is empty. By using a pump instead of a capillary wick or any other passive medium to draw liquid, only the actually required amount of liquid aerosol-forming substrate may be transported to the heating element. Liquid aerosol-forming substrate may only be pumped upon demand, for example by a request for a puff by a vaper.

In at least one example embodiment, the aerosol-generating system further comprises a chamber into which the liquid aerosol-forming substrate is delivered. The heating element is arranged inside the chamber and is downstream of the outlet of the liquid storage portion.

As used herein, the terms 'upstream', 'downstream', 'proximal', 'distal', 'front' and 'rear', are used to describe the relative positions of elements, or portions of elements, of the aerosol-generating system in relation to the direction in which a vaper draws on the aerosol-generating system during vaping.

The aerosol-generating system may comprise a mouth end through an aerosol exits the aerosol-generating system. The mouth end may also be referred to as the proximal end. During vaping, a vaper draws on the proximal or mouth end of the aerosol-generating system. The aerosol-generating system comprises a distal end opposed to the proximal or mouth end. The proximal or mouth end of the aerosol-generating system may also be referred to as the downstream end and the distal end of the aerosol-generating system may also be referred to as the upstream end. Elements, or portions of elements, of the aerosol-generating system may be described as being upstream or downstream of one another based on their relative positions between the proximal, downstream or mouth end and the distal or upstream end of the aerosol-generating system.

In at least one example embodiment, the aerosol-generating system further comprises a tubing segment through which the liquid aerosol-forming substrate is delivered from the liquid storage portion to the atomizer. The atomizer is downstream of an open end of the tubing segment.

The tubing segment, also referred to as tube, may be a nozzle. The tubing segment may comprise any appropriate material, for example glass, metal, for example stainless steel, or plastics material, for example polyetheretherketone (PEEK). In at least one example embodiment, the tube may have a diameter of about 1 millimetre to about 2 millimetres, but other sizes are possible. In at least one example embodiment, the tubing segment comprises a capillary tube. The cross-section of the capillary tube may be generally circular, ellipsoid, triangular, rectangular or any other suitable shape to convey liquid. At least a width dimension of the cross-sectional area of the capillary tube is chosen to be sufficiently small such that on the one hand capillary forces are present. At the same time, the cross-sectional area of the capillary tube is sufficiently large such that a suitable amount of liquid aerosol-forming substrate can be conveyed to the heating element. The cross-sectional area of the capillary tube is below about 4 square millimetres, below about 1 square millimetre, or below about 0.5 square millimetres.

The heating element may comprise a heating coil extending from the tubing segment in longitudinal direction. In at least one example embodiment, the heating coil may be mounted transverse to the tubing segment. The heating coil may overlap with the open end of the tubing segment for up to about 3 millimetres or up to about 1 millimetre. In at least one example embodiment, there may be a distance between the open end of the tubing segment and the heating coil. The length of the heating coil may be about 2 millimetres to about 9 millimetres or about 3 millimetres to about 6 millimetres. The diameter of the heating coil may be chosen such that one end of the heating coil can be mounted around the tubing segment. The diameter of the heating coil may be about 1 millimetre to about 5 millimetres, or about 2 millimetres to about 4 millimetres.

In at least one example embodiment, the aerosol-generating system comprises a main unit and a cartridge. The cartridge is removably coupled to the main unit. The main unit comprises a power supply. The liquid storage portion is provided in the cartridge. The pump is in the main unit. In at least one example embodiment, the main unit further comprises the atomizer. The main unit may comprise a tubing segment.

The aerosol-generating system may comprise a power supply, such as a battery, within the main body of the housing. In at least one example embodiment, the power supply may be another form of charge storage device such as a capacitor. The power supply may require recharging and may have a capacity that allows for the storage of enough energy for one or more vaping experiences. In at least one example embodiment, the power supply may have sufficient capacity to allow for the continuous generation of aerosol for a period of about six minutes or for a period that is a multiple of about six minutes. In at least one example embodiment, the power supply may have sufficient capacity to allow for an estimated desired (or, alternatively predetermined) number of puffs or discrete activations of the heater assembly.

For allowing ambient air to enter the aerosol-generating system, a wall of the housing of the aerosol-generating system, such as a wall opposite the atomizer or a bottom wall, is provided with at least one semi-open inlet or air inlet. The semi-open inlet allows air to enter the aerosol-generating system. The wall may not allow air or liquid to leave the aerosol-generating system through the semi-open inlet. A semi-open inlet may be a semi-permeable membrane that is permeable in one direction only for air, but is air- and liquid-tight in the opposite direction. A semi-open inlet may be a one-way valve. In at least one example embodiment, the semi-open inlets allow air to pass through the inlet only if specific conditions are met, for example a minimum depression in the aerosol-generating system or a volume of air passing through the valve or membrane.

The liquid aerosol-forming substrate is a substrate configured to release volatile compounds that can form an aerosol. The volatile compounds may be released by heating the liquid aerosol-forming substrate. The liquid aerosol-forming substrate may comprise plant-based material. The liquid aerosol-forming substrate may comprise tobacco. The liquid aerosol-forming substrate may comprise a tobacco-containing material containing volatile tobacco flavour compounds, which are released from the liquid aerosol-forming substrate upon heating. The liquid aerosol-forming substrate may alternatively comprise a non-tobacco-containing material. The liquid aerosol-forming substrate may comprise homogenized plant-based material. The liquid aerosol-forming substrate may comprise homogenized tobacco material. The liquid aerosol-forming substrate may comprise at least one aerosol-former. The liquid aerosol-forming substrate may comprise other additives and ingredients, such as flavourants.

The aerosol-generating system may be an electrically operated aerosol-generating system. In at least one example embodiment, the aerosol-generating system is portable. The aerosol-generating system may have a size comparable to a cigar or cigarette. The aerosol-generating system may have a total length ranging from about 30 millimetres to about 150 millimetres. The aerosol-generating system may have an external diameter ranging from about 5 millimetres to about 30 millimetres.

The cartridge may be a disposable article to be replaced with a new cartridge once the liquid storage portion of the cartridge is empty or below a minimum volume threshold. In at least one example embodiment, the cartridge is pre-loaded with liquid aerosol-forming substrate. The cartridge may be refillable.

The aerosol-generating system may be in a preheat mode when the aerosol-generating system has been powered on. The electric circuitry heats the heating element constantly until the heating element reaches a desired (or, alternatively predetermined) operating temperature. The operating temperature may be about 250° C. The duration of the preheat mode may be controlled by the preheat duration parameter. In at least one example embodiment, the preheat duration parameter is set to a value ranging from about 3 seconds to about 4 seconds. Under normal conditions, the aerosol-generating system may reach its operating temperature within the preheat duration. Once the operating temperature is reached, the pump may be activated for at least one pump cycle to transport an adjusted amount of liquid aerosol-forming substrate through the pump to make the aerosol-generating system ready to use.

The aerosol-generating system may then enter the temperature hold mode until the electric circuitry detects a puff or until a hold timeout duration is reached as defined by the value of the hold timeout duration parameter.

In temperature hold mode, a sequence of heating pulses may be sent to the heating element which can have the effect of maintaining a lower preheat temperature below the operating temperature until the hold timeout is reached. The lower preheat temperature may be about 150° C.

Once a puff has been detected and the heating element has reached the operating temperature, the controller may activate the pump and set an adjusted flow rate for delivering liquid aerosol-forming substrate to the deposition region of the heating element for the duration of the puff. The flow rate depends upon the puff intensity.

Once the puff stops, the aerosol-generating system may return to the temperature hold mode. If no input is detected during the temperature hold duration, the device may automatically cool down and wait for input.

FIG. 1 is an illustration of an aerosol-generating system. The aerosol-generating system comprises a main body with a housing 2. Within the housing 2, a liquid storage portion 4 is provided. The liquid storage portion 4 holds a liquid aerosol-forming substrate 6. The liquid storage portion 4 is not part of the main body and may be provided as a cartridge which can be disposed when the liquid aerosol-forming substrate 6 in the liquid storage portion 4 is depleted. After disposal of the liquid storage portion 4, a new liquid storage portion 4 is inserted into the housing 2.

The main body of the aerosol-generating system comprises a battery 8, which is connected to a controller 10. The controller 10 is configured to control the flow of electric current from the battery 8 via conductors 12 to a heating element 14 of a vaporizer. The controller 10 is further connected to a pump 16, which is provided to pump liquid aerosol-forming substrate 6 from the liquid storage portion 4 to the heating element 14 of the vaporizer. The pump 16 is configured as a micropump inside the main body of the aerosol-generating system.

The aerosol-generating system further comprises a pressure or airflow sensor 22, which is arranged in an airflow path 19 near an air inlet 18. The sensor 22 is configured to detect the airflow and/or pressure of the air within the airflow path 19, which is drawn by a vaper towards a mouth end 20 of the aerosol-generating system. In this regard, the sensor 22 detects an airflow rate or pressure drop in the airflow path 19 and the controller 10 determines the puff intensity based upon the sensor 22 reading after 0.5 seconds after the puff initiation. In at least one example embodiment, the controller 10 compares the output from the sensor 22 with values of airflow rates and/or pressures contained in a look-up table that may be stored in a memory. The airflow rate denotes the amount of air per unit of time that flows through the airflow path 19.

The controller 10 is configured to adjust the delivery flow rate of liquid aerosol-forming substrate 6 from the liquid storage portion 4 to the heating element 14 of the vaporizer.

The controller 10 increases the delivery flow rate if a high puff intensity is determined and decreases the delivery flow rate if a low puff intensity is determined. A high puff intensity is determined by the controller 10 when a high airflow rate or a high pressure drop is determined based on the output from the sensor 22.

In at least one example embodiment, the controller 10 is further configured to control the heating temperature of the heating element 14 of the vaporizer. The controller 10 increases the heating temperature if a high puff intensity is determined and decreases the heating temperature if a low puff intensity is determined.

After a puff initiation is detected by the sensor or a button, which the vaper presses, the controller controls the pump 16 to pump the liquid aerosol-forming substrate 6 from the liquid storage portion 4 to the heating element 14 of the vaporizer. The controller 10 adjusts the delivery flow rate based upon the determined puff intensity. The liquid aerosol-forming substrate 6 is vaporized by the vaporizer to form an aerosol. The aerosol is formed by mixing of the vaporized liquid aerosol-forming substrate 6 with ambient air which is drawn through the air inlet 18. The generated aerosol is subsequently inhaled by a vaper through the mouth end 20.

Figure 2:
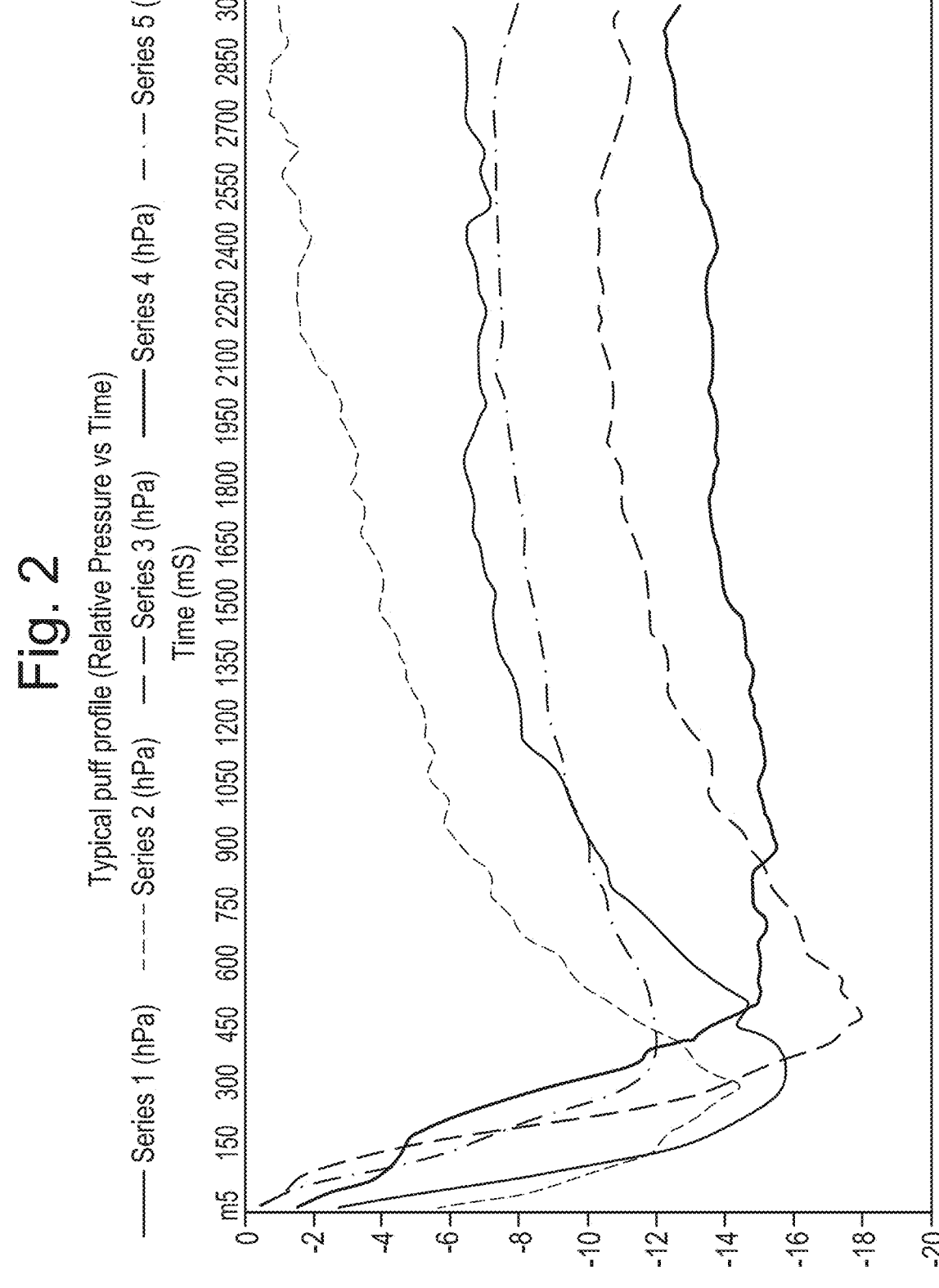
FIG. 2 is a graph showing experimental measurements of the relative pressure within an aerosol-generating system during a puff according to at least one example embodiment.

FIG. 2 shows a diagram of measurements of pressure drop values, measured in hectopascal (1 hPa=100 Pa), over the time, measured in milliseconds, of a puff. The different measurements show that around about 0.3 seconds to about 0.6 seconds, and around about 0.5 seconds after the initiation of the puff, the pressure difference is the highest. After that, the pressure difference slowly decreases. Thus, the controller determines the puff intensity by evaluating the sensor measurement after about 0.5 seconds after the puff initiation.

The exemplary embodiments described above illustrate but are not limiting. In view of the above discussed exemplary embodiments, other embodiments consistent with the above exemplary embodiments will now be apparent to one of ordinary skill in the art.

We claim:

1. An aerosol-generating system, the system comprising:
   a pump configured to deliver an aerosol-forming substrate;
   a puff sensor in an airflow path, the puff sensor configured to sense a puff; and
   a controller configured to determine a puff intensity based on an output from the puff sensor and adjust a delivery flow rate of the pump in response to the determined puff intensity.

2. The aerosol-generating system of claim 1, wherein the puff sensor is a pressure sensor.

3. The aerosol-generating system of claim 1, further comprising:
   a storage portion configured to contain the aerosol-forming substrate, the pump configured to pump the aerosol-forming substrate from the storage portion.

4. The aerosol-generating system of claim 1, wherein the pump is a micropump.

5. The aerosol-generating system of claim 1, further comprising:
   a housing including,
      an air inlet, and
      an air outlet.

6. The aerosol-generating system of claim 5, further comprising:
   a heating element configured to vaporize the aerosol-forming substrate, the pump configured to deliver the aerosol-forming substrate to the heating element.

7. The aerosol-generating system of claim 6, wherein the heating element is a heating coil.

8. The aerosol-generating system of claim 7, wherein the heating coil extends in a longitudinal direction.

9. The aerosol-generating system of claim 7, wherein the heating coil extends in a transverse direction.

10. The aerosol-generating system of claim 7, wherein the controller is further configured to adjust electrical power supplied to the heating element in response to the determined puff intensity.

\* \* \* \* \*